(12) United States Patent
Addison et al.

(10) Patent No.: US 10,499,818 B2
(45) Date of Patent: Dec. 10, 2019

(54) SYSTEM AND METHOD FOR PROVIDING BLOOD PRESSURE SAFE ZONE INDICATION DURING AUTOREGULATION MONITORING

(71) Applicant: COVIDIEN LP, Mansfield, MA (US)

(72) Inventors: Paul Stanley Addison, Edinburgh (GB); James N. Watson, Edinburgh (GB); Dean Montgomery, Edinburgh (GB)

(73) Assignee: Covidien LP, Mansfield, MA (US)

( * ) Notice: Subject to any disclaimer, the term of this patent is extended or adjusted under 35 U.S.C. 154(b) by 566 days.

(21) Appl. No.: 15/296,150

(22) Filed: Oct. 18, 2016

(65) Prior Publication Data

US 2017/0105631 A1 Apr. 20, 2017

Related U.S. Application Data

(60) Provisional application No. 62/243,341, filed on Oct. 19, 2015.

(51) Int. Cl.
*A61B 5/02* (2006.01)
*A61B 5/0205* (2006.01)
(Continued)

(52) U.S. Cl.
CPC ............ *A61B 5/0205* (2013.01); *A61B 5/021* (2013.01); *A61B 5/026* (2013.01);
(Continued)

(58) Field of Classification Search
CPC ......... A61B 5/0205; A61B 5/00; A61B 5/021; A61B 5/026; A61B 5/145; A61B 5/1455;
(Continued)

(56) References Cited

U.S. PATENT DOCUMENTS 4,776,339 A 10/1988 Schreiber
5,351,685 A 10/1994 Potratz
(Continued)

FOREIGN PATENT DOCUMENTS

EP 615723 A1 9/1994
WO WO9843071 A1 10/1998
(Continued)

OTHER PUBLICATIONS

International Preliminary Report on Patentability from International Application No. PCT/US2016/057443, dated Apr. 24, 2018, 8 pp.
(Continued)

*Primary Examiner* — Eric J Messersmith
(74) *Attorney, Agent, or Firm* — Shumaker & Sieffert, P.A.

(57) ABSTRACT

A method for monitoring autoregulation includes, using a processor, using a processor to execute one or more routines on a memory. The one or more routines include receiving one or more physiological signals from a patient, determining a correlation-based measure indicative of the patient's autoregulation based on the one or more physiological signals, and generating an autoregulation profile of the patient based on autoregulation index values of the correlation-based measure. The autoregulation profile includes the autoregulation index values sorted into bins corresponding to different blood pressure ranges. The one or more routines also include designating a blood pressure range encompassing one or more of the bins as a blood pressure safe zone indicative of intact regulation and providing a signal to a display to display the autoregulation profile and a first indicator of the blood pressure safe zone.

21 Claims, 7 Drawing Sheets

(51) Int. Cl.

| | |
|---|---|
| *A61B 5/021* | (2006.01) |
| *A61B 5/026* | (2006.01) |
| *A61B 5/145* | (2006.01) |
| *A61B 5/1455* | (2006.01) |
| *A61B 5/00* | (2006.01) |
| *G16H 40/63* | (2018.01) |
| *G16H 50/30* | (2018.01) |
| *G16H 50/20* | (2018.01) |
| *A61B 5/03* | (2006.01) |

(52) U.S. Cl.
CPC ...... *A61B 5/02028* (2013.01); *A61B 5/14546* (2013.01); *A61B 5/14553* (2013.01); *A61B 5/4064* (2013.01); *A61B 5/7246* (2013.01); *A61B 5/742* (2013.01); *A61B 5/743* (2013.01); *A61B 5/7425* (2013.01); *G16H 40/63* (2018.01); *G16H 50/20* (2018.01); *G16H 50/30* (2018.01); *A61B 5/0059* (2013.01); *A61B 5/0261* (2013.01); *A61B 5/031* (2013.01)

(58) Field of Classification Search
CPC .............. A61B 5/7246; A61B 5/14553; A61B 5/14546; A61B 5/743; A61B 5/742; A61B 5/02028; A61B 5/4064; A61B 5/7425; A61B 5/0059; A61B 5/0261; A61B 5/031; G16H 50/20; G16H 40/63; G16H 50/30

See application file for complete search history.

(56) References Cited

U.S. PATENT DOCUMENTS

| | | | |
|---|---|---|---|
| 5,482,034 | A | 1/1996 | Lewis et al. |
| 5,533,507 | A | 7/1996 | Potratz |
| 5,577,500 | A | 11/1996 | Potratz |
| 5,584,296 | A | 12/1996 | Cui et al. |
| 5,626,140 | A | 5/1997 | Feldman et al. |
| 5,803,910 | A | 9/1998 | Potratz |
| 5,934,277 | A | 8/1999 | Mortz |
| 6,385,471 | B1 | 5/2002 | Mortz |
| 6,438,399 | B1 | 8/2002 | Kurth |
| 6,453,183 | B1 | 9/2002 | Walker |
| 6,505,060 | B1 | 1/2003 | Norris |
| 6,510,329 | B2 | 1/2003 | Heckel |
| 6,599,251 | B2 | 7/2003 | Chen et al. |
| 6,668,182 | B2 | 12/2003 | Hubelbank |
| 6,714,803 | B1 | 3/2004 | Mortz |
| 6,754,516 | B2 | 6/2004 | Mannheimer |
| 6,896,661 | B2 | 5/2005 | Dekker |
| 6,987,994 | B1 | 1/2006 | Mortz |
| 7,001,337 | B2 | 2/2006 | Dekker |
| 7,221,969 | B2 | 5/2007 | Stoddart et al. |
| 7,268,873 | B2 | 9/2007 | Sevick-Muraca et al. |
| 7,744,541 | B2 | 6/2010 | Baruch et al. |
| 8,556,811 | B2 | 10/2013 | Brady |
| 2004/0097797 | A1 | 5/2004 | Porges et al. |
| 2005/0004479 | A1 | 1/2005 | Townsend et al. |
| 2005/0033129 | A1 | 2/2005 | Edgar, Jr. et al. |
| 2005/0192488 | A1 | 9/2005 | Bryenton et al. |
| 2005/0192493 | A1 | 9/2005 | Wuori |
| 2007/0004977 | A1 | 1/2007 | Norris |
| 2007/0049812 | A1 | 3/2007 | Aoyagi et al. |
| 2008/0081974 | A1 | 4/2008 | Pav |
| 2008/0146901 | A1 | 6/2008 | Katura et al. |
| 2008/0200785 | A1 | 8/2008 | Fortin |
| 2008/0228053 | A1 | 9/2008 | Wang et al. |
| 2009/0326386 | A1 | 12/2009 | Sethi et al. |
| 2010/0010322 | A1 | 1/2010 | Brady |
| 2010/0030054 | A1 | 2/2010 | Baruch et al. |
| 2010/0049082 | A1 | 2/2010 | Hu et al. |
| 2011/0046459 | A1 | 2/2011 | Zhang et al. |
| 2011/0077490 | A1* | 3/2011 | Simpson ............ A61B 5/14532 600/345 |
| 2011/0105912 | A1 | 5/2011 | Widman et al. |
| 2012/0149994 | A1 | 6/2012 | Luczyk et al. |
| 2012/0253211 | A1 | 10/2012 | Brady et al. |
| 2012/0271130 | A1 | 10/2012 | Benni |
| 2013/0190632 | A1 | 7/2013 | Baruch et al. |
| 2014/0073888 | A1 | 3/2014 | Sethi et al. |
| 2014/0275818 | A1 | 9/2014 | Kassem et al. |
| 2014/0278285 | A1 | 9/2014 | Marmarelis et al. |
| 2016/0106372 | A1 | 4/2016 | Addison et al. |
| 2016/0324425 | A1 | 11/2016 | Addison et al. |
| 2016/0345913 | A1 | 12/2016 | Montgomery et al. |
| 2016/0367197 | A1 | 12/2016 | Addison et al. |
| 2017/0000395 | A1 | 1/2017 | Addison et al. |
| 2017/0000423 | A1 | 1/2017 | Addison et al. |
| 2017/0095161 | A1 | 4/2017 | Addison et al. |
| 2017/0105672 | A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | 2016/182853 A1 | 11/2016 |
| WO | WO2016182853 A1 | 11/2016 |

OTHER PUBLICATIONS

International Search Report and Written Opinion from PCT Application No. PCT/US2016/057443 dated Jan. 24, 2017, 15 pp.
U.S. Appl. No. 15/666,167, filed Aug. 1, 2017, naming inventors Addison et al.
Chuan et al., "Is cerebrovascular autoregulation associated with outcomes after major noncardiac surgery? A prospective observational pilot study," Acta Anaesthesiol Scand., Aug. 5, 2018, 10 pp.
Monica Williams, et al.,; "Intraoperative blood pressure and Cerebral perfusion: strategies to clarify hemodynamic goals," Paediatric Anaesthesia, vol. 24, No. 7, Jul. 12, 2014; pp. 657-667; XP055331904.
Celeste Dias, et al.: "Optimal Cerebral Perfusion Pressure Management at Bedside: a Single-Center Pilot Study," Neurocritical care, vol. 23, No. 1, Jan. 8, 2015; pp. 92-102; ISSN: 1541-6933.
International Search Report and Written Opinion for PCT Application No. PCT/US2016/057443 dated Jan. 24, 2017, 14 pgs.
Addison, P. S., et al.; "Low-Oscillation Complex Wavelets," Journal of Sound and Vibration, 2002, vol. 254, Elsevier Science Ltd., pp. 1-30.
Addison, P. S.; "The Illustrated Wavelet Transform Handbook," 2002, IOP Publishing Ltd., Bristol, UK, Ch. 2.
Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).
Barreto, Armando B., et al.; "Adaptive LMS Delay Measurement in dual Blood Volume Pulse Signals for Non-Invasive Monitoring," *IEEE*, pp. 117-120 (1997).
Bassan, Haim, et al.; "Identification of pressure passive cerebral perfusion and its mediators after infant cardiac surgery," Pediatric Research Foundation, vol. 57, No. 1, 2005; pp. 35-41.
Belal, Suliman Yousef, et al.; "A fuzzy system for detecting distorted plethysmogram pulses in neonates and paediatric patients," *Physiol. Meas.*, vol. 22, pp. 397-412 (2001).
Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.
Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.
Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

(56) References Cited

OTHER PUBLICATIONS

Brady, Ken M., et al.; "Noninvasive Autoregulation Monitoring with and without Intracranial Pressure in a Naïve Piglet Brain," Neuroscience in Anesthesiology and Perioperative Medicine, 2010, vol. 111, No. 1, International Anesthesia Research Society, pp. 191-195.
Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.
Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.
Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012)
Chan, K.W., et al.; "17.3: Adaptive Reduction of Motion Artifact from Photoplethysmographic Recordings using a Variable Step-Size LMS Filter," IEEE, pp. 1343-1346 (2002)+A10.
Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.
Chen, Liangyou, et al.; "IS respiration-induced variation in the photoplethysmogram associated with major hypovolemia in patients with actue tramatic injuries," SHOCK, vol. 34, No. 5, pp. 455-460 (2010).
Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.
Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.
Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.
Cysewska-Sobusaik, Anna; "Metrological Problems With noninvasive Transillumination of Living Tissues," *Proceedings of SPIE*, vol. 4515, pp. 15-24 (2001).
Czosnyka, Marek, et al.; "Monitoring of cerebrovascular autoregulation: Facts, Myths, and Missing Links," Neurocrit Care (2009) 10:373-386.
Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.
Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.
Dias, Celeste, et al.; "Optimal Cerebral Perfusion Pressure Management at Bedside: a Single-Center Pilot Study," Neurocritical care, vol. 23, No. 1, Jan. 8, 2015; pp. 92-102; ISSN: 1541-6933.
East, Christine E., et al.; "Fetal Oxygen Saturation and Uterine Contractions During Labor," *American Journal of Perinatology*, vol. 15, No. 6, pp. 345-349 (Jun. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.
Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.

Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.
Ge, Z.; "Significance tests for the wavelet cross spectrum and wavelet linear coherence," Annales Geophysicae, 2008, 26, Copernicus Publications on behalf of European Geosciences Union, pp. 3819-3829.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Goldman, Julian M.; "Masimo Signal Extraction Pulse Oximetry," *Journal of Clinical Monitoring and Computing*, vol. 16, pp. 475-483 (2000).
Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.
Hamilton, Patrick S., et al.; "Effect of Adaptive Motion-Artifact Reduction on QRS Detection," *Biomedical Instrumentation & Technology*, pp. 197-202 (May-Jun. 2000).
Huang, J., et al.; "Low Power Motion Tolerant Pulse Oximetry," Anesthesia & Analgesia 2002 94: S103.
Johansson, A.; "Neural network for photoplethysmographic respiratory rate monitoring," *Medical & Biological Engineering & Computing*, vol. 41, pp. 242-248 (2003).
Kaestle, S.; "Determining Artefact Sensitivity of New Pulse Oximeters in Laboratory Using Signals Obtained from Patient," *Biomedizinische Technik*, vol. 45 (2000).
Kim, J.M., et al.; "Signal Processing Using Fourier & Wavelet Transform for pulse oximetry," pp. II-310-II-311 (2001).
Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).
Leahy, Martin J., et al.; "Sensor Validation in Biomedical Applications," *IFAC Modelling and Control in Biomedical Systems*, Warwick, UK; pp. 221-226 (1997).
Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.
Lee, Jennifer K., et al.; A pilot study of cerebrovascular reactivity autoregulation after pediatric cardiac arrest, Resuscitation 85, 2014, Elsevier Ireland Ltd., pp. 1387-1393.
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.
Mcgrath, S.P., et al.; "Pulse oximeter plethysmographic waveform changes in awake, spontaneously breathing, hypovolemic volunteers," Anesth. Analg. vol. 112 No. 2, pp. 368-374 (2010).
Montgomery, Dean, et al.; "Data cluestering methods for the determination of cerebral autoregulation functionality," Journal of Clinical Monitoring and Computing, vol. 30, No. 5, Sep. 16, 2015, pp. 661-668.
Morren, G., et al.; "Detection of autoregulation in the brain of premature infants using a novel subspace-based technique," 23rd Annual International Conference of IEEE Engineering in Medicine and Biology Society, Oct. 2001; pp. 1-4.
Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.
Neumann, R., et al.; "Fourier Artifact suppression Technology Provides Reliable $SpO_2$," Anesthesia & Analgesia 2002, 94: S105.

(56) References Cited

OTHER PUBLICATIONS

Obrig, Hellmuth, et al.; "Spontaneous low frequency oscillations of cerebral heodynamics and metabolism in human adults," NeuroImage 12, 623-639 (2000).
Odagiri, Y.; "Pulse Wave Measuring Device," *Micromechatronics*, vol. 42, No. 3, pp. 6-11 (published Sep. 1998) (Article in Japanese—contains English summary of article).
Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.
Panerai, B.; "Cerebral Autoregulation: from models to clinical Applications," Cardiovascular Engineering: an International Journal, vol. 8, No. 1, Nov. 28, 2007, (28 pgs.).
Payne, Stephen J., et al.; "Tissue Oxygenation Index as a Measure of Cerebral Autoregulation," Biomedial Engineering, Feb. 2004, Innsbruck, Austria, pp. 546-550.
Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.
Reinhard, Matthias, et al.; "Oscillatory cerebral hemodynamics-the macro-vs. microvascular level," Journal of the Neurological Sciences 250 (2006) 103-109.
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.
Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.
Shamir, M., et al.; "Pulse oximetry plethysmographic waveform during changes in blood volume," British Journal of Anaesthesia 82(2): 178-81 (1999).
Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.
Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.
Such, Hans Olaf; "Optoelectronic Non-invasive Vascular Diagnostics Using multiple Wavelength and Imaging Approach," *Dissertation*, (1998).
Todd, Bryan, et al.; "The Identification of Peaks in Physiological Signals," *Computers and Biomedical Research*, vol. 32, pp. 322-335 (1999).
Tsuji, Miles, et al.; "Cerebral intravascular oxygenation correlates with mean arterial pressure in critically ill premature infants," American Academy of Pediatrics, 2000; 106; pp. 625-632.
Wagner, Bendicht P., et al.; "Dynamic cerebral autoregulatory response to blood pressure rise measured by near-infrared spectroscopy and intracranial pressure," Critical Care Medicine 2002, vol. 30, No. 9, pp. 2014-2021.
Whitaker, E., et al.; "Cerebrovascular Autoregulation After Pediatric Cardiac Arrest," NEURO-85, 2012, 2 pgs.
Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.
Wong, Flora Y., et al.; "Impaired Autoregulation in preterm infants identified by using spatially resolved spectroscopy," American Academy of Pediatrics DOI:10.1542 (2008) e604-611.
Wu Dongmei, et al.; "$Na^*/H^*$ Exchange inhibition delays the onset of hypovolemic circulatory shock in pigs," SHOCK, vol. 29, No. 4, pp. 519-525 (2008).
Wu, et al.; "Using synchrosqueezing transform to discover breathing dynamics from ECG signals," arXiv:1105.1571, vol. 2, Dec. 2013, pp. 1-9.
Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.
Zhang, Rong, et al.; "Transfer function analysis of dynamic cerebral autoregulation in humans," 1998 the American Physiological Society; pp. H233-H241.
Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.
U.S. Appl. No. 15/648,665, filed Jul. 13, 2017, Dean Montgomery.

\* cited by examiner

SYSTEM AND METHOD FOR PROVIDING BLOOD PRESSURE SAFE ZONE INDICATION DURING AUTOREGULATION MONITORING

BACKGROUND

The present disclosure relates generally to medical devices and, more particularly, to systems and methods for monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on various physiological signals. However, existing systems may not provide the patient's autoregulation status and/or changes in the patient's autoregulation status in an effective manner.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
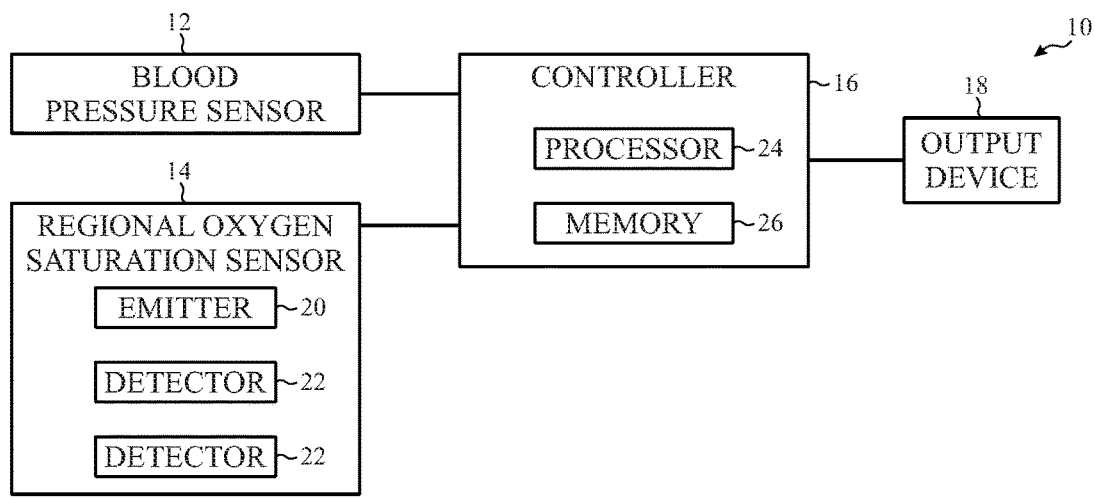
FIG. 1 is a block diagram of an embodiment of a system for monitoring a patient's autoregulation.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In some cases, a patient's autoregulation may be monitored via correlation-based measures (e.g., autoregulation indices) indicative of the patient's autoregulation function. For example, near-infrared spectroscopy (NIRS)-based indices may be utilized as measures of autoregulation. Autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) indicative of the patient's autoregulation status may be derived based at least in part on a linear correlation between the patient's blood pressure and oxygen saturation. In addition, autoregulation may be monitored by correlating measurements of the patient's blood pressure with measurements of blood flow. In particular, a hemoglobin volume index (HVx) indicative of the patient's autoregulation may be derived based at least in part on a linear correlation between the patient's blood pressure and blood flow. Further, non-NIRS-based indices may be utilized as measures of autoregulation, such as mean velocity index (Mx).

The disclosed systems and methods may utilize an autoregulation index to generate and display an autoregulation profile (e.g., autoregulation index values sorted into bins corresponding to different blood pressure ranges) of the patient. The measures of autoregulation may be NIRS-based indices (e.g., COx, HVx, etc.) or non-MRS-based indices (e.g., Mx) utilized by the systems and methods. The autoregulation profile may include the autoregulation plotted on a vertical axis and the blood pressures plotted on the horizontal axis. A negative autoregulation index value may indicate intact autoregulation within a particular blood pressure range, while a positive autoregulation index value may indicate impaired autoregulation within a particular blood pressure range. In addition, the system may generate a blood pressure (BP) safe zone (i.e., designate a blood pressure range encompassing one or more of the bins) indicative of intact autoregulation. If there is insufficient patient data (e.g., autoregulation index measurements and blood pressure measurements) of the patient, an initial BP safe zone may be generated utilizing historical population data (e.g., based on patient specific inputs) and/or initially measured baseline physiological parameters (e.g., mean arterial pressure (MAP), heart rate, respiration rate, regional oxygen saturation ($rSO_2$), etc.) of the patient. Once there is sufficient patient data, a patient specific BP safe zone may be generated based on the patient's autoregulation index measurements and blood pressure measurements. A graphical indicator of the BP safe zone may be overlaid on the corresponding one or more bins of the autoregulation profile. If the patient's current blood pressure measurement falls outside of the zone, the system may provide an alarm (e.g., audible or visual indication).

The system may display other information along with the autoregulation profile and the BP safe zone. For example, a BP history may be displayed. The BP history may include bins of blood pressure ranges corresponding to the bins in the autoregulation profile plotted on a horizontal axis and a count relating to time spent in (or out of) the BP safe zone on a vertical axis. The count may represent an amount or percentage of time in the BP safe zone, a number of times in the BP safe zone, or a number of times out of the BP safe zone. In certain embodiments, the graphical indicator of the BP safe zone may also overlay the bins of BP history that correspond to the bins of the autoregulation profile within the BP safe zone. In addition, the system may display a BP signal (e.g., plot of a BP signal segment (i.e., BP value over time)).

The system may also display an indicator of a target blood pressure (TBP). The TBP may represent a blood pressure value or a range of values at which the patient's autoregulation function is greatest and/or may be useful for clinical management of a patient's blood pressure. For example, the target blood pressure may guide a healthcare provider's treatment of the patient (e.g., provide an indication of whether the healthcare provider should administer medication to lower the patient's blood pressure or to raise the patient's blood pressure to reach the TBP within the intact autoregulation zone). For example, the TBP may be displayed in a variety of ways (e.g., point, number, vertical line, etc.). In certain embodiments, the system may indicate a distance of the patient's measured blood pressure from the TBP. The distance may be indicated via a gradiated color change of the indicator of the TBP or a blip bar.

In certain embodiments, the TBP is provided to the system. In other embodiments, the system generates the TBP. In certain situations, it may be beneficial to identify autoregulation zones indicative of a patient's blood pressure dependent autoregulation status. A patient's autoregulation system may typically function well over a certain range of blood pressures. Accordingly, each patient typically exhibits at least three autoregulation zones: a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. For example, although the blood pressures at which the autoregulation system functions properly may vary by patient, a particular patient may exhibit a lower impaired autoregulation zone associated with relatively low blood pressures of less than approximately 60 mmHg at which the patient's autoregulation function is impaired, an intact autoregulation zone associated with intermediate blood pressures between approximately 60 and 150 mmHg at which the patient's autoregulation system works properly, and an upper impaired autoregulation zone associated with relatively high blood pressures above approximately 150 mmHg at which the patient's autoregulation function is impaired. It may be advantageous to identify the patient's autoregulation zones and/or to determine an upper limit of autoregulation (ULA) value and/or a lower limit of autoregulation (LLA) that approximately define an upper and a lower blood pressure (e.g., MAP) boundary, respectively, within which autoregulation is generally intact and functioning properly. Blood pressures approximately above the ULA and/or approximately below the LLA may be associated with impaired autoregulation function.

In some embodiments, the systems and methods may be configured to determine a TBP for the patient based on an $rSO_2$-BP curve, the LLA, and/or ULA. In some embodiments, the TBP may be a blood pressure value along the $rSO_2$-BP curve equidistant from the LLA and ULA within the intact autoregulation zone. In other embodiments, the TBP may be a point of the $rSO_2$-BP curve within the intact autoregulation zone closest to either the LLA or the ULA depending on if the clinical consequences would be worse dropping below the LLA or exceeding the ULA. Alternatively, the TBP may be determined based on the gradients of the $rSO_2$-BP curve (e.g., gradient of the curve blow the LLA and/or the gradient of the curve above the ULA). In some embodiments, the TBP may be determined based on error bars associated within the LLA and/or ULA. In other embodiments, the TBP may be determined by a point of inflection.

As discussed in more detail below, the systems and methods may be configured to utilize the BP safe zone and/or the TBP. In some embodiments, the system may be configured to provide information indicative of the autoregulation status, the BP safe zone, and/or the TBP to an operator. Such systems and methods may in turn provide improved patient monitoring and patient care.

FIG. 1 is a block diagram of an embodiment of a system 10 for monitoring a patient's autoregulation. As shown, the system 10 includes a blood pressure sensor 12, an oxygen saturation sensor 14 (e.g., a regional oxygen saturation sensor), a controller 16, and an output device 18. The blood pressure sensor 12 may be any sensor or device configured to obtain the patient's blood pressure (e.g., MAP). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable identification of the autoregulation zone(s) and to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex). In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. The emitter 20 may be driven to emit light by light drive circuitry of a monitor (e.g., a specialized monitor having a controller configured to control the light drive circuitry). In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed. Surface data (e.g., from the skin) may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status. While the depicted oxygen saturation sensor 14 is a regional saturation sensor, the sensor 14 may be a pulse oximeter configured to obtain the patient's oxygen saturation or may be any suitable sensor configured to provide a signal indicative of the patient's blood flow. For example, the sensor 14 may be configured to emit light at a single wavelength (e.g., an isobestic wavelength) and to provide a signal indicative of blood flow.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to determine the autoregulation zone(s) and/or to evaluate the patient's cerebral autoregulation status. Alternatively, the controller 16 may be configured to process the blood pressure signal and the blood volume signal to evaluate the patient's cerebral autoregulation status. In some embodiments, the controller 16 may be part of a specialized monitor and/or may be configured to control operation of (e.g., control light drive circuitry to drive the emitter 20 of the oxygen saturation sensor 14) and/or receive signals directly from the blood pressure sensor 12 and/or the oxygen saturation sensor 14. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

The controller 16 may be configured to determine one or more autoregulation index values (e.g., COx, HVx, etc.). In some embodiments, the controller 16 may be configured to determine a COx based on the blood pressure signal and the oxygen saturation signal. The COx is generally indicative of vascular reactivity, which is related to cerebral blood vessels' ability to control proper blood flow, via vasoconstriction (a narrowing of the blood vessel) and/or vasodilation (expansion of the blood vessel), for example. The controller 16 may derive a COx value by determining a linear correlation between blood pressure measurements and oxygen saturation measurements. The linear correlation may be based on a Pearson coefficient, for example. The Pearson coefficient may be defined as the covariance of the measured blood pressure (e.g., arterial blood pressure or MAP) and oxygen saturation divided by the product of their standard deviations. The result of the linear correlation may be a regression line between the blood pressure measurements and the oxygen saturation measurements, and the slope of the regression line may be generally indicative of the patient's autoregulation status. In one possible implementation, a regression line with a relatively flat or negative slope (e.g., blood pressure increases after regional oxygen saturation decreases) may suggest that cerebral autoregulation is working properly, while a regression line with a positive slope (e.g., blood pressure remains the same or decreases after regional oxygen saturation decreases) may suggest that the cerebral autoregulation is impaired. Thus, if the regression line has negative slope, the COx value is between −1 and 0. If the regression line has a positive slope, the COx value is between 0 and 1.

In some embodiments, the controller 16 may be configured to determine an HVx based on the blood pressure signal and the blood volume signal. The HVx represents the relationship between relative tissue hemoglobin and MAP. HVx is based on the assumption that autoregulatory dilation and vasoconstriction produce changes in cerebral blood volume that are proportional to changes in relative tissue hemoglobin. The controller 16 may derive an HVx value by determining a linear correlation between blood pressure measurements and blood volume measurements. The linear correlation may be based on a Pearson coefficient, for example. The Pearson coefficient may be defined as the covariance of the measured blood pressure (e.g., arterial blood pressure or MAP) and oxygen saturation divided by the product of their standard deviations. The result of the linear correlation may be a regression line between the blood pressure measurements and the blood volume measurements, and the slope of the regression line may be generally indicative of the patient's autoregulation status. In one possible implementation, a regression line with a relatively flat or negative slope (e.g., blood pressure increases after blood volume decreases) may suggest that cerebral autoregulation is working properly, while a regression line with a positive slope (e.g., blood pressure remains the same or decreases after blood volume decreases) may suggest that the cerebral autoregulation is impaired. Thus, if the regression line has negative slope, the HVx value is between −1 and 0. If the regression line has a positive slope, the HVx value is between 0 and 1.

The controller 16 may be configured to generate and display (via an output device 18 such as a display) an autoregulation profile (e.g., autoregulation index values sorted into bins corresponding to different blood pressure ranges) of the patient based on the autoregulation index values and the blood pressure measurements. The autoregulation profile may include the autoregulation index values plotted on a vertical axis and the blood pressures plotted on the horizontal axis. A negative autoregulation index value may indicate intact autoregulation within a particular blood pressure range, while a positive autoregulation index value may indicate impaired autoregulation within a particular blood pressure range. In addition, the controller 16 may generate a BP safe zone (i.e., designate a blood pressure range encompassing one or more of the bins) indicative of intact autoregulation. If there is insufficient patient data (e.g., autoregulation index measurements and blood pressure measurements) of the patient, the controller 16 may generate an initial BP safe zone utilizing historical population data (e.g., based on patient specific inputs such as age, sex, body mass index (BMI), etc.) and/or initially measured baseline physiological parameters (e.g., mean arterial pressure (MAP), heart rate, respiration rate, regional oxygen saturation ($rSO_2$), etc.) of the patient. Once there is sufficient patient data, the controller 16 may generate a patient specific BP safe zone based on the patient's autoregulation index measurements and blood pressure measurements. A graphical indicator of the BP safe zone may be overlaid the corresponding one or more bins of the autoregulation profile.

The controller 16 may generate and display other information along with the autoregulation profile and the BP safe zone. For example, a BP history may be displayed. The BP history may include bins of blood pressure ranges corresponding to the bins in the autoregulation profile plotted on a horizontal axis and a count relating to time spent in (or out of) the BP safe zone on a vertical axis. The count may represent an amount or percentage of time in the BP safe zone, a number of times in the BP safe zone, or a number of times out of the BP safe zone. In certain embodiments, the graphical indicator of the BP safe zone may also overlay the bins of BP history that correspond to the bins of the autoregulation profile within the BP safe zone. In addition, the controller 16 may display a BP signal (e.g., plot of a BP signal segment (i.e., BP value over time)) via the output device 18 (e.g., display).

The controller 16 may also cause display of an indicator of TBP via the output device 18. The TBP may represent a blood pressure value or a range of values at which the patient's autoregulation function is greatest and/or may be useful for clinical management of a patient's blood pressure. For example, the target blood pressure may guide a healthcare provider's treatment of the patient (e.g., provide an indication of whether the healthcare provider should administer medication to lower the patient's blood pressure or to raise the patient's blood pressure to reach the TBP within the intact autoregulation zone). For example, the TBP may be displayed in a variety of ways (e.g., point, number, vertical line, etc.). In certain embodiments, the controller 16 may indicate a distance of the patient's measured blood pressure from the TBP via the output device 18. The distance may be indicated via a gradiated color change (e.g., from green to amber to red, where green represents a closer distance, amber an intermediate distance, and red a farther distance) of the indicator of the TBP or a blip bar.

In certain embodiments, the controller 16 receives an input of the TBP. In other embodiments, the controller 16 (e.g., via algorithms) generates the TBP. In some embodiments, the controller 16 is configured to determine the TBP for the patient based on an $rSO_2$-BP curve, the LLA, and/or ULA. In some embodiments, the TBP may be a blood pressure value along the $rSO_2$-BP curve equidistant from the LLA and ULA within the intact autoregulation zone. In other embodiments, the TBP may be a point of the $rSO_2$-BP curve within the intact autoregulation zone closest to either the LLA or the ULA depending on if the clinical consequences would be worse dropping below the LLA or exceeding the ULA. Alternatively, the TBP may be determined based the gradients of the $rSO_2$-BP curve (e.g., gradient of the curve blow the LLA and/or the gradient of the curve above the ULA). In some embodiments, the TBP may be determined based on error bars associated within the LLA and/or ULA. In other embodiments, the TBP may be determined by a point of inflection.

In the illustrated embodiment, the controller 16 includes a processor 24 and a memory device 26. The controller 16 may also include one or more storage devices. As discussed in more detail below, the processor 24 may be used to execute code stored in the memory device 26 or other suitable computer-readable storage medium or memory circuitry, such as code for implementing various monitoring functionalities. The processor 24 may be used to execute software, such as software for carrying out any of the techniques disclosed herein, such as processing the blood pressure signals, blood volume signals, and/or oxygen saturation signals, determining a COx value, determining a HVx value, determining the TBP, identifying autoregulation zones, identifying the LLA and/or the ULA, causing display of information related to the autoregulation profile, the BP history, the BP safe zone, and/or the status on a display, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for processing the blood pressure signals, blood volume signals, and/or oxygen saturation signals, determining a COx value, determining a HVx value, determining the TBP, identifying autoregulation zones, identifying the LLA and/or the ULA, causing display of information related to the autoregulation profile, the BP history, the BP safe zone, and/or the status on a display, and so forth. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the blood pressure signal, the oxygen saturation signal, the COx, the HVx, the BP safe zone, the autoregulation profile, the BP history, the TBP, etc.), instructions (e.g., software or firmware for processing the blood pressure signals, blood volume signals, and/or oxygen saturation signals, determining a COx value, determining a HVx value, determining the TBP, identifying autoregulation zones, identifying the LLA and/or the ULA, causing display of information related to the autoregulation profile, the BP history, the BP safe zone, and/or the status on a display, and so forth), predetermined thresholds, and any other suitable data.

As shown, the system 10 includes the output device 18. In some embodiments, the controller 16 may be configured to provide signals indicative of the autoregulation profile, the BP history, the BP safe zone, the TBP, the current blood pressure, the distance of current blood pressure from the TBP, and/or the patient's autoregulation status (e.g., current blood pressure relative to the BP safe zone) to the output device 18. As discussed in more detail below, the controller 16 may be configured to generate an alarm signal indicative of the patient's autoregulation status and to provide the alarm signal to the output device 18. For example, in certain embodiments, if the current blood pressure of the patient falls outside of the BP safe zone, the controller 16 may provide an alarm (e.g., audible or visual indication) via the output device 18. In certain embodiments, the alarm may be provided via the flashing of portions of the display (e.g., the autoregulation profile, the BP safe zone, the BP history, and/or the BP signal). The alarm may also be provided via changing a color of the BP safe zone indicative of a blood pressure within the BP safe zone (e.g., green) to a different color indicative of a blood pressure outside of the BP safe zone (e.g., red). An intermediate color (e.g., yellow or orange) may be utilized to indicate a blood pressure (within the BP safe zone) approaching an outer limit out of the BP safe zone. In certain embodiments, the alarm may differentiate between a blood pressure below the BP safe zone and a blood pressure above the BP safe zone. This differentiation may be provided via two different beeps (one representative of blood pressure below the BP safe zone and one representative of blood pressure above the BP safe zone) provided via the output device 18 (e.g., speaker). The beeps may differ in tones, durations, volume, tunes, or other types of audible features.

The output device 18 may include any device configured to receive signals (e.g., signals indicative of the autoregulation profile, the BP history, the BP signal, the BP safe zone, the TBP, the distance between the current blood pressure and the TBP, the alarm signal, or the like) from the controller 16 and visually and/or audibly output information indicative of the patient's autoregulation status (e.g., the autoregulation profile, the BP history, the BP signal, the BP safe zone, the TBP, the distance between the current blood pressure and the TBP, the alarm signal, a text message, a color, or the like). For instance, the output device 18 may include a display configured to provide a visual representation of the autoregulation profile, the BP history, the BP signal, the BP safe zone, the TBP, the distance between the current blood pressure and the TBP, the alarm signal, or the like as determined by the controller 16. Additionally or alternatively, the output device 18 may include an audio device configured to provide sounds (e.g., spoken message, beeps, or the like) indicative of the patient's the autoregulation profile, the BP history, the BP signal, the BP safe zone, the TBP, the distance between the current blood pressure and the TBP, the alarm signal, or the like. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a specialized computer or monitor).

Figure 2:
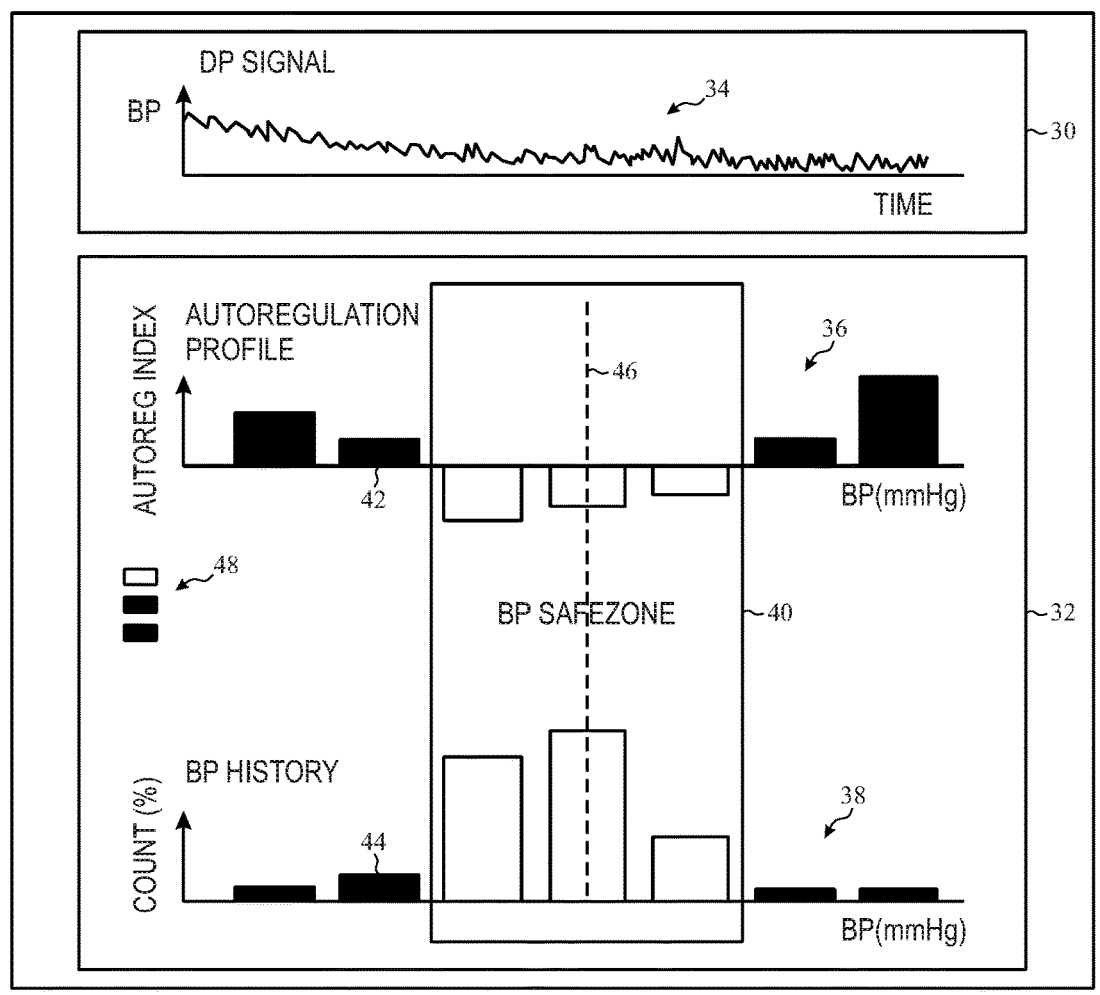
FIG. 2 is an example of a display configured to display an autoregulation status of a patient (e.g., having a blood pressure safe zone)

FIG. 2 illustrates an example of a display 28 of an autoregulation status of a patient (e.g., displayed on the output device 18). The display 28 includes a BP signal area 30 and an autoregulation area 32. As depicted, the BP signal area 30 is located above the autoregulation area 32. In other embodiments, the BP signal area 30 may be located below the autoregulation area 32 or both areas 30, 32 may be shown side by side. The BP signal area 30 includes a plot 34 of a segment of a BP signal (most recent BP signal) received from the patient. The plot 34 includes the blood pressure value (BP) plotted on the vertical axis and time plotted along the horizontal axis.

The autoregulation area 32 includes autoregulation information such as an autoregulation profile 36, a BP history 38 of the patient, and a BP safe zone 40. The autoregulation profile 36 is generated based on blood pressure measurements and autoregulation index values (e.g., HVx, COx, Mx, etc.) obtained from the patient. In the autoregulation profile 36, the autoregulation index values are sorted into bins corresponding to different blood pressure ranges as represented by bars 42. The autoregulation profile 36 includes the autoregulation index values plotted along the vertical axis and blood pressures on the horizontal axis. Bars 42 extending above the horizontal axis indicate positive autoregulation index values suggesting that the cerebral autoregulation is impaired, while bars 42 extending below the horizontal axis indicate negative autoregulation index values suggesting that the cerebral autoregulation works properly. In certain embodiments, the bins (or bars 42) associated with a positive autoregulation index value may be displayed as a different color (e.g., red) than a color (green) of the bins associated with a negative autoregulation index value. As depicted, the number of bins (or bars 42) is 7. However, the number of bins may vary based on the width of each bin. Each bin may have a width of 5 mmHg units. In particular, binning measurements may be associated with grouping certain measurements such that each bin may include or represent a certain number of original data measurements. For example, each bin may be representative of a number of original measurements that fall within a particular interval or width. It should be noted that the width or interval of the bin may be a pre-defined value stored within the memory device 26, and the width or interval of the bin may be any value greater than 0 mmHg units, between approximately 0 and 3 mmHg units, between approximately 3 and 5 mmHg units, or greater than 5 mmHg units. In certain embodiments, the width of each bin may be determined based on a quality or an amount of data received from the sensors. In addition, each bin may include or represent any number of original measurements or samples. For example, in certain situations, the bin may represent 1-5 samples, 5-10 samples, 10-20 samples, 20-50 samples, or more than 50 samples. In certain embodiments, the number of samples that each bin represents may be dependent on the quality of samples obtained, a sampling rate of the sensors, a signal quality metric, and/or any combination thereof.

Figure 3:
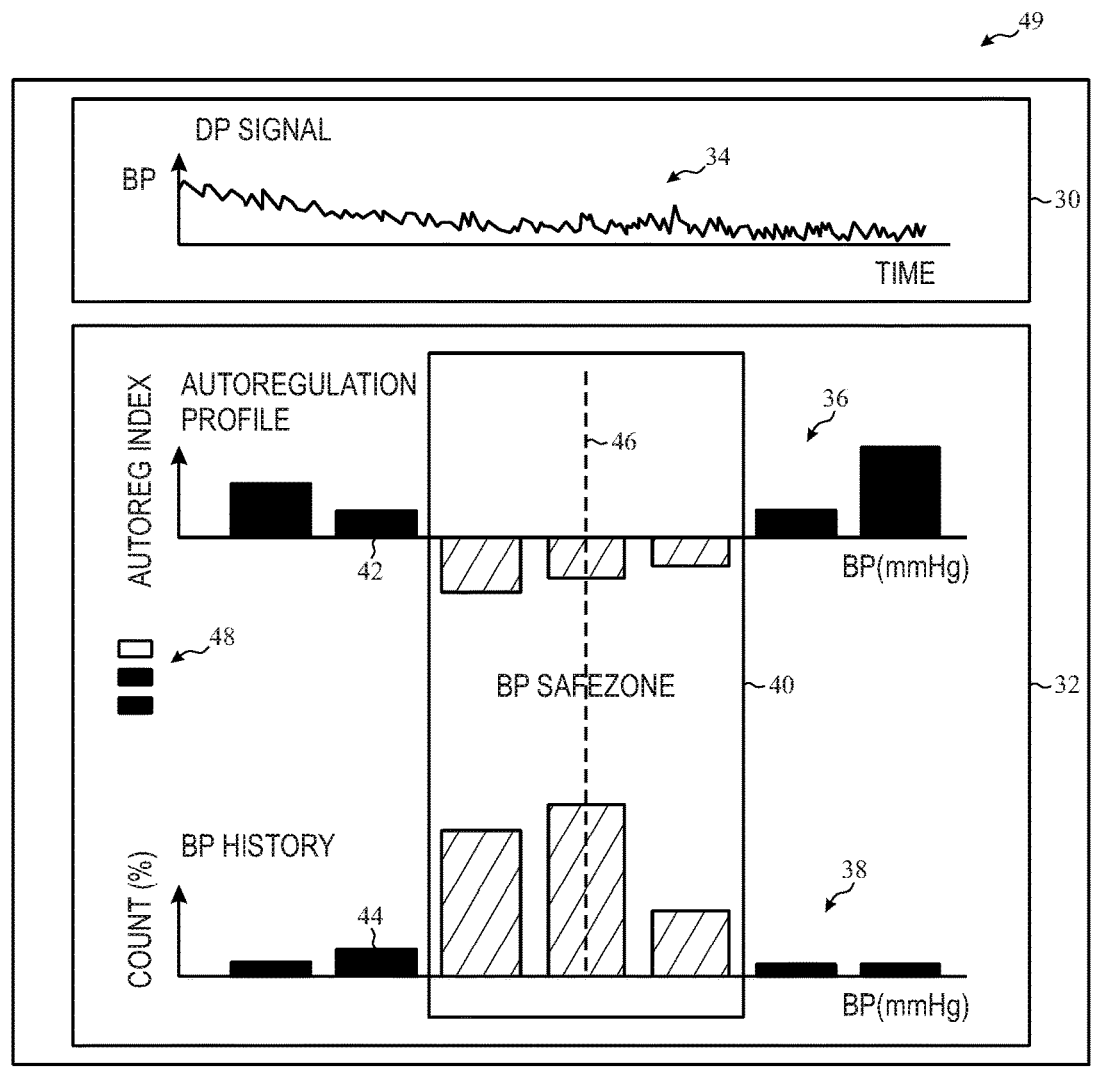
FIG. 3 is an example of a display configured to display an autoregulation status of a patient (e.g., having a preliminary blood pressure safe zone)

The BP safe zone 40 designates a blood pressure range encompassing one or more of the bins indicative of intact autoregulation. The BP safe zone 40 may be overlaid or encompass the corresponding one or more bins of the autoregulation profile 36. In certain embodiments, it may take a number of minutes to build up a useful picture of the autoregulation function. For example, it may take 30 minutes in the operating room or 3 to 4 hours in the intensive care unit to experience enough blood pressure changes to build up the autoregulation profile 36. While the autoregulation profile 36 is being built, the BP safe zone 40 may have a color (e.g., yellow, see display 49 of FIG. 3) different than a color (e.g., green) of the BP safe zone 40 once enough data has been obtained to build the autoregulation profile 36. Alternatively, the bars 42, 44 within the BP safe zone 40 may have different markings once enough data has been obtained. For example, in FIG. 2 the bars 42, 44 within the BP safe zone 40 have no hatching, while the bars 42, 44 on display 49 of FIG. 3 have hatching. For example, the BP safe zone 40 may be colored yellow until a preset criterion is reached and change to green upon reaching that criterion. The criterion may be forming enough bars (e.g., as least 4 bars 42 or any other predetermined number of bars 42). Alternatively, the criterion may be based on an amount of data collected. For example, a single bar 42 may be sufficient if the bar 42 has enough data. In embodiments, where the BP safe zone 40 is colored, the BP safe zone 40 may be transparent enough to visualize the bars 42 and their respective color. In some embodiments, a textual indicator (e.g., "Building Autoregulation Profile", "Autoregulation Profile Complete", etc.) may be displayed indicating the status of the building of the Autoregulation Profile.

In certain embodiments, if there is insufficient data (e.g., autoregulation index measurements and blood pressure measurements) from the patient, the controller 16 may generate an initial BP safe zone 40 utilizing historical population data (e.g., based on patient specific inputs such as age, sex, body mass index, etc.) and/or initially measured baseline physiological parameters (e.g., mean arterial pressure (MAP), heart rate, respiration rate, regional oxygen saturation ($rSO_2$), etc.) of the patient. Once there is sufficient patient data, the controller 16 may generate a patient specific BP safe zone 40 (e.g., subsequent BP safe zone 40) based on the patient's autoregulation index measurements and blood pressure measurements. The initial BP safe zone 40 may have a color (e.g., yellow, see FIG. 3) different than a color (e.g., green, see FIG. 2) of the patient specific BP safe zone 40.

The BP history 38 may be generated based on the blood pressure measurements and the autoregulation index values (e.g., HVx, COx, Mx, etc.) obtained from the patient. The BP history 38 may include bins (e.g., bars 44) of blood pressure ranges corresponding to the bins (e.g., bars 42) in the autoregulation profile 36 plotted on a horizontal axis and a count relating to time spent in the BP safe zone 40 on a vertical axis. The count may represent an amount or percentage of time blood pressure measurements are in the BP safe zone 40, a number of times blood pressure measurements are in the BP safe zone 40, or a number of times blood pressure measurements are out of the BP safe zone 40. In certain embodiments, the BP safe zone 40 may also overlay the bins of the BP history 38 that correspond to the bins of the autoregulation profile 36 within the BP safe zone 40. In certain embodiments, the bins (bars 44) of the BP history 38 that correspond with the bins (e.g., bars 42) having a positive autoregulation index value may be displayed as a different color (e.g., red) than a color (green) of the bins (bars 44) of the BP history 38 that correspond with the bins (e.g., bars 42) associated with a negative autoregulation index value.

In certain embodiments, an indicator 46 may be displayed in the BP signal area 30 or the autoregulation area 32 (as depicted in FIG. 2) representing the TBP. The TBP may be received by the controller 16 (e.g., via operator input) or may be determined by the controller 16 as described in greater detail below. The indicator 46 may include a vertical line (as depicted in FIG. 2), a number (e.g., in mmHg), or a point. In certain embodiments, an indicator 48 may be displayed in the BP signal area 30 or the autoregulation area 32 (as depicted in FIG. 2) representing a distance of a current blood pressure measurement of the patient from the TBP. In certain embodiments, the indicator 48 may include a blip bar (as depicted in FIG. 2) that increases (e.g., fills up) as the distance increases between the current blood pressure measurement and the TBP or decreases (e.g., empties) as the distance decreases between the current blood pressure measurement and the TBP. Alternatively, the indicator 46 of the TBP may undergo a gradiated color change (e.g., from green (smaller distance) to amber (intermediate distance) to red (greater distance)) as the distance between the current blood pressure and the TBP changes.

In certain embodiments, if the current blood pressure of the patient falls outside of the BP safe zone 40, the controller 16 may provide an alarm (e.g., visual indication) via the display 28. In certain embodiments, the alarm may be provided via the flashing of portions of the display 28 (e.g., the autoregulation profile 36, the BP safe zone 40, the BP history 38, and/or the BP signal 34). The alarm may also be provided via changing a color of the BP safe zone 40 indicative of a blood pressure within the BP safe zone 40 (e.g., green) to a different color indicative of a blood pressure outside of the BP safe zone 40 (e.g., red). An intermediate color (e.g., yellow or orange) may be utilized to indicate a blood pressure (within the BP safe zone 40) approaching an outer limit out of the BP safe zone 40. In certain embodiments, the alarm may differentiate between a blood pressure below the BP safe zone 40 and a blood pressure above the BP safe zone 40 utilizing different colors for the BP safe zone 40. In certain embodiments, a textual alarm may be provided on the display 28 (e.g., "Blood Pressure Outside BP Safe Zone", "Blood Pressure Approaching Being Outside the BP Safe Zone", etc.).

Figure 4:
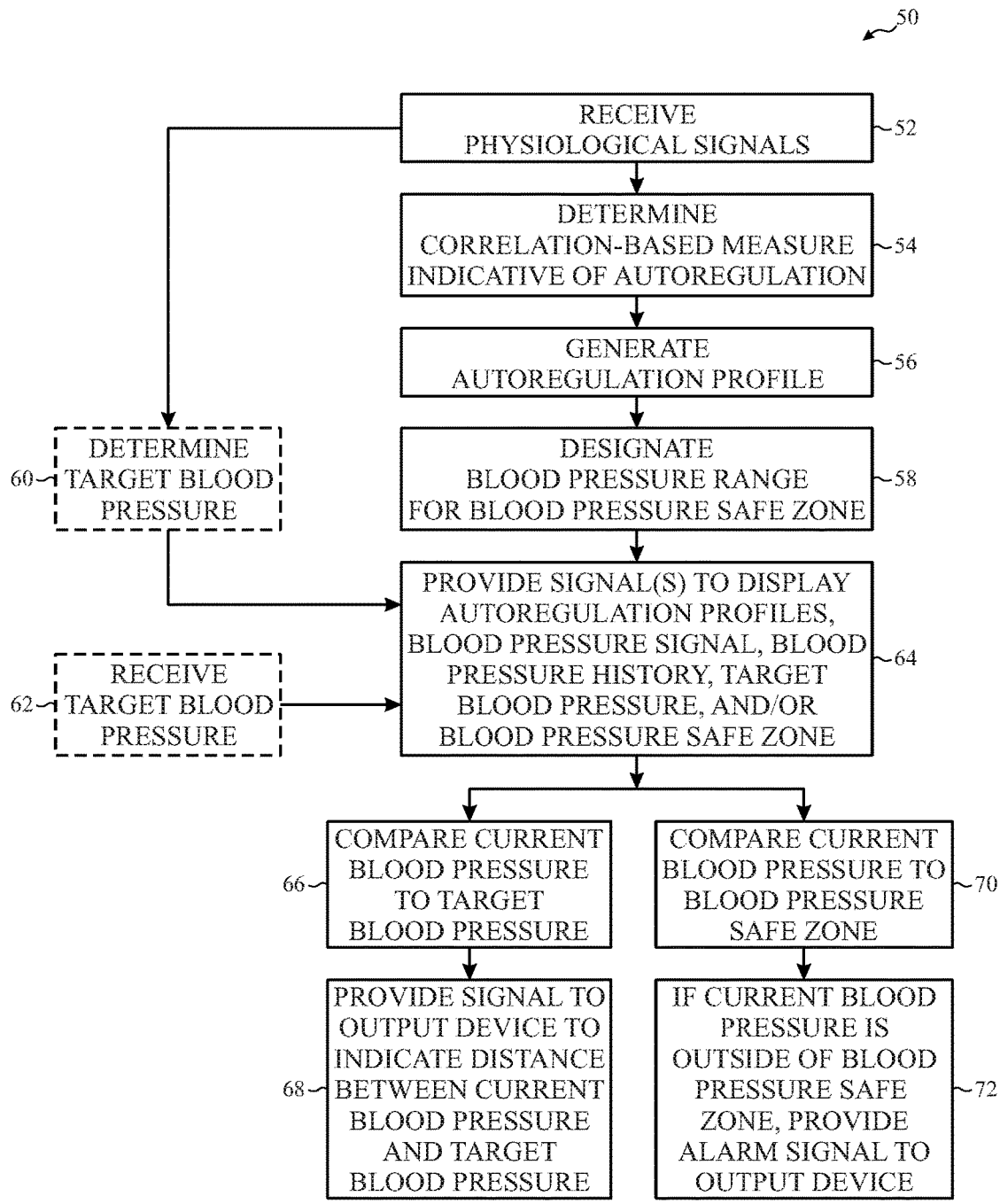
FIG. 4 is a process flow diagram of a method of monitoring autoregulation that includes designating a blood pressure safe zone, in accordance with an embodiment.

FIG. 4 is a process flow diagram of a method 50 of monitoring autoregulation that includes designating a BP safe zone. The method 50 includes various steps represented by blocks. The method 50 may be performed as an automated procedure by a system, such as system 10. For example, some or all of the steps of the method 50 may be implemented by the controller 16 (e.g., the processor 24 of the controller 16). Although the flow chart illustrates the steps in a certain sequence, it should be understood that the steps may be performed in any suitable order, certain steps may be carried out simultaneously, and/or certain steps may be omitted, where appropriate. In addition, insofar as steps of the method 50 disclosed herein are applied to the received signals, it should be understood that the received signals may be raw signals or processed signals. That is, the method 50 may be applied to an output of the received signals.

In step 52, the controller 16 may receive physiological signals. For example, the controller 16 may receive the blood pressure signal (e.g., arterial blood pressure signal). In some embodiments, the controller 16 may receive the blood pressure signal from the blood pressure sensor 12, as set forth above. In some embodiments (if COx is utilized for the autoregulation index), the controller 16 may receive the oxygen saturation signal (e.g., regional oxygen saturation signal) from the regional oxygen saturation sensor 14. In some embodiments (if HVx is utilized for the autoregulation index), the controller 16 may receive the blood volume signal from the regional oxygen saturation sensor 14.

In step 54, the controller 16 determines a correlation-based measure indication of autoregulation (e.g., autoregulation index values such as HVx, COx, Mx, etc.) based on the received physiological signals. In step 56, the controller 16 generates the autoregulation profile based on the autoregulation index values of the correlation based measure and the blood pressure signal. As noted above, the autoregulation profile includes the autoregulation index values sorted into bins corresponding to different pressure ranges. In step 58, the controller 16 designates a blood pressure range for the BP zone. As noted above, in certain embodiments, if there is insufficient patient data (e.g., autoregulation index measurements and blood pressure measurements) of the patient, the controller 16 may generate an initial BP safe zone utilizing historical population data (e.g., based on patient specific inputs such as age, sex, body mass index, etc.) and/or initially measured baseline physiological parameters (e.g., mean arterial pressure (MAP), heart rate, respiration rate, regional oxygen saturation ($rSO_2$), etc.) of the patient. Once there is sufficient patient data, the controller 16 may generate a patient specific BP safe zone (e.g., subsequent BP safe zone) based on the patient's autoregulation index measurements and blood pressure measurements.

In step 60, in certain embodiments, the controller 16 determines the TBP as described in greater detail below. Alternatively, in other embodiments, in step 62, the controller 16 receives the TBP. In step 64, the controller 16 provides one or more signals to display the autoregulation profile, the BP signal, the BP history, the TBP, and/or the BP safe zone on the output device 18 (e.g., display) as described above. In step 66, the controller 16 compares the patient's current blood pressure (derived from the blood pressure signal) to the TBP. In step 68, the controller 16 provides a signal to display an indication of a distance between the current blood pressure and the TBP. As noted above, a blip bar may be utilized or an indicator of the TBP may undergo a gradiated color change.

In step 70, the controller 16 compares the patient's current blood pressure (derived from the blood pressure signal) to the BP safe zone. In step 72, if the patient's current blood pressure is outside of the BP safe zone, the controller 16 provides an alarm signal to the output device 18 (e.g., display and/or speaker). The alarm may include a visual or audible alarm. In certain embodiments, the alarm may be provided via the flashing of portions of the display (e.g., the autoregulation profile, the BP safe zone, the BP history, and/or the BP signal). The alarm may also be provided via changing a color of the BP safe zone indicator indicative of a blood pressure within the BP safe zone indicator (e.g., green) to a different color indicative of a blood pressure outside of the BP safe zone indicator (e.g., red). An intermediate color (e.g., yellow or orange) may be utilized to indicate a blood pressure (within the BP safe zone) approaching an outer limit out of the BP safe zone. In certain embodiments, the alarm may differentiate between a blood pressure below the BP safe zone and a blood pressure above the BP safe zone utilizing different colors for the BP safe zone. In certain embodiments, a textual alarm may be provided on the display (e.g., "Blood Pressure Outside BP Safe Zone", "Blood Pressure Approaching Being Outside the BP Safe Zone", etc.). In other embodiments, the alarm may differentiate between a blood pressure below the BP safe zone and a blood pressure above the BP safe zone utilizing two different beeps (one representative of blood pressure below the BP safe zone and one representative of blood pressure above the BP safe zone) via a speaker. The beeps may differ in tones, durations, volume, tunes, or other types of audible features.

Figure 5:
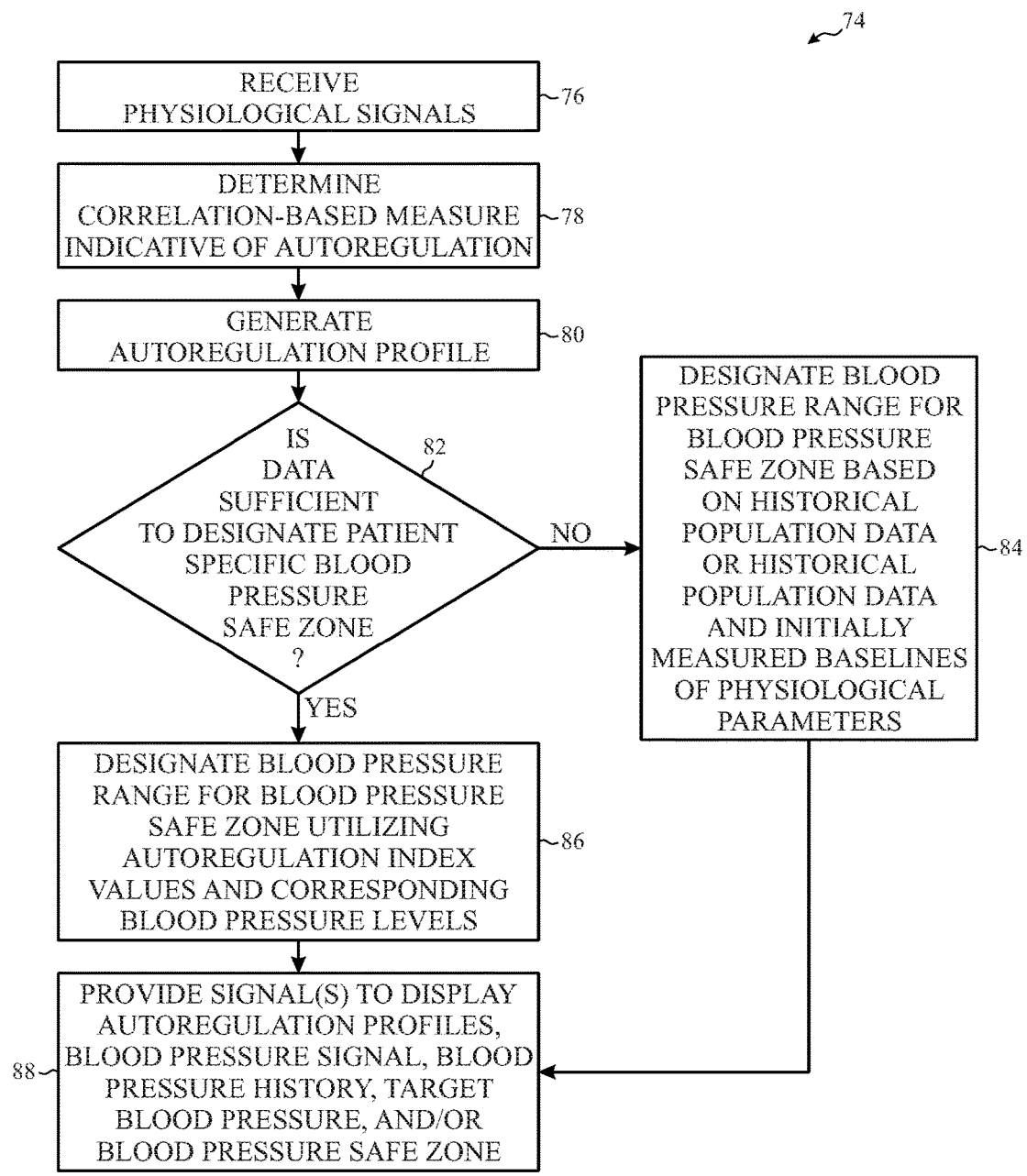
FIG. 5 is a process flow diagram of a method of monitoring autoregulation that includes determining how to designate a blood pressure safe zone, in accordance with an embodiment.

FIG. 5 is a process flow diagram of a method 74 of monitoring autoregulation that includes determining how to designate a blood pressure safe zone. The method 74 includes various steps represented by blocks. The method 74 may be performed as an automated procedure by a system, such as system 10. For example, some or all of the steps of the method 74 may be implemented by the controller 16 (e.g., the processor 24 of the controller 16). Although the flow chart illustrates the steps in a certain sequence, it should be understood that the steps may be performed in any suitable order, certain steps may be carried out simultaneously, and/or certain steps may be omitted, where appropriate. In addition, insofar as steps of the method 74 disclosed herein are applied to the received signals, it should be understood that the received signals may be raw signals or processed signals. That is, the method 74 may be applied to an output of the received signals.

In step 76, the controller 16 may receive physiological signals. For example, the controller 16 may receive the blood pressure signal (e.g., arterial blood pressure signal). In some embodiments, the controller 16 may receive the blood pressure signal from the blood pressure sensor 12, as set forth above. In some embodiments (if COx is utilized for the autoregulation index), the controller 16 may receive the oxygen saturation signal (e.g., regional oxygen saturation signal) from the regional oxygen saturation sensor 14. In some embodiments (if HVx is utilized for the autoregulation index), the controller 16 may receive the blood volume signal from the regional oxygen saturation sensor 14.

In step 78, the controller 16 determines a correlation-based measure indication of autoregulation (e.g., autoregulation index values such as HVx, COx, Mx, etc.) based on the received physiological signals. In step 80, the controller 16 generates the autoregulation profile based on the autoregulation index values of the correlation based measure and the blood pressure signal. As noted above, the autoregulation profile includes the autoregulation index values sorted into bins corresponding to different pressure ranges.

In step 82, the controller 16 determines if there is sufficient data (e.g., autoregulation index measurements and blood pressure measurements) of the patient to designate a patient specific BP safe zone. If there is insufficient patient data (e.g., autoregulation index measurements and blood pressure measurements) of the patient, in step 84, the controller 16 may designate an initial BP safe zone utilizing historical population data (e.g., based on patient specific inputs such as age, sex, body mass index, etc.) and/or initially measured baseline physiological parameters (e.g., mean arterial pressure (MAP), heart rate, respiration rate, regional oxygen saturation ($rSO_2$), etc.) of the patient. If there is sufficient patient data or once there is sufficient patient data, in step 86, the controller 16 may generate a patient specific BP safe zone (e.g., subsequent BP safe zone) based on the patient's autoregulation index measurements and corresponding blood pressure measurements. In step 88, the controller 16 provides one or more signals to display the autoregulation profile, the BP signal, the BP history, the TBP, and/or the BP safe zone on the output device 18 (e.g., display) as described above. In certain embodiments, the controller 16 may perform additional steps such as those described above in FIG. 5.

Figure 6:
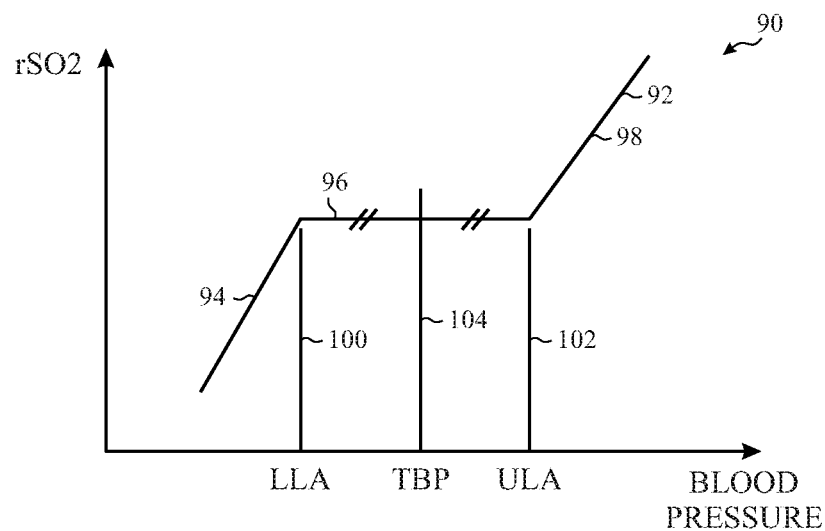
FIG. 6 is an example of a graph illustrating a regional oxygen saturation ($rSO_2$)-blood pressure (BP) curve derived from regional oxygen saturation values and blood pressure values (e.g., having a target blood pressure derived from the $rSO_2$-BP curve)

As mentioned above, the TBP may be determined by the controller 16, in particular, utilizing an $rSO_2$-BP curve. In particular, it may be desirable to determine the TBP somewhere within the region defined by the LLA and ULA. FIG. 6 is an example of a graph 90 illustrating an $rSO_2$-BP curve 92 derived from regional oxygen saturation values on the vertical axis and blood pressure (e.g., arterial blood pressure) values (e.g., having a target blood pressure derived from the $rSO_2$-BP curve 92) on the horizontal axis. As depicted, the $rSO_2$-BP curve 92 is an ideal curve. In particular, the curve 92 includes (from left to right) a positive gradient portion 94 (e.g., indicative of impaired autoregulation), a horizontal plateau 96 (e.g., indicative of intact autoregulation), and another positive gradient portion 98 (e.g., indicative of impaired autoregulation). The LLA (represented by line 100) separates the positive gradient portion 94 from the horizontal plateau 96. The ULA (represented by line 102) separates the horizontal plateau 96 from the positive gradient portion 98. As described above, cerebral autoregulation occurs over a range of blood pressures between the LLA and the ULA. As depicted in FIG. 6, the controller 16 determines the TBP by designating a point (represented by line 104) equidistant between the LLA and ULA along the curve 92.

In certain embodiments, the controller 16 determines the TBP by designating a point nearer the ULA if the clinical consequences of dropping below the LLA are more severe for the patient than if the ULA is exceeded. In other embodiments, the controller 16 determines the TBP by designating a point nearer the LLA if the clinical consequences of exceeding the ULA are more severe for the patient than dropping below the LLA.

Figure 7:
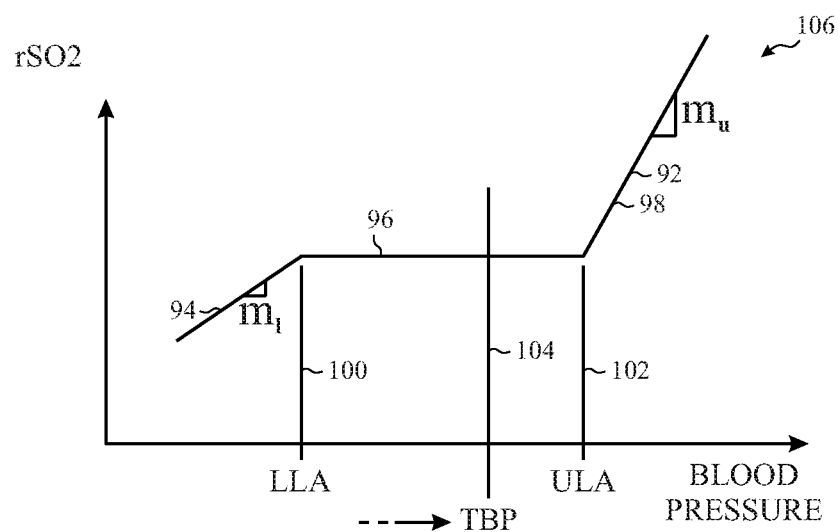
FIG. 7 is an example of a graph illustrating an $rSO_2$-BP curve derived from regional oxygen saturation values and blood pressure values (e.g., having a target blood pressure derived from gradients of the $rSO_2$-BP curve)

In certain embodiments, gradients of the curve 92 may be utilized in determining the TBP. FIG. 7 is an example of a graph 106 illustrating the $rSO_2$-BP curve 92 and the utilization of gradients to determine the TBP. The controller 16 may determine a gradient portion, $m_l$, for the positive gradient portion 94 of the curve 92. The controller 16 may also determine a gradient portion, $m_u$, for the positive gradient portion 98 of the curve 92. In certain embodiments, the controller 16 weights the TBP towards a higher gradient portion as it may be better defined in terms of the $rSO_2$-BP relationship. For example, the TBP (represented by line 104) may be shifted toward ULA since $m_u$ has a higher gradient than $m_l$ as depicted in FIG. 7. In other embodiments, the controller 16 weights the TBP towards a lower gradient portion as deviations from the TBP during a procedure may have less effect on the cerebral oxygenation. For example, the TBP may be shifted toward the LLA since $m_l$ may have a higher gradient than $m_u$.

Figure 8:
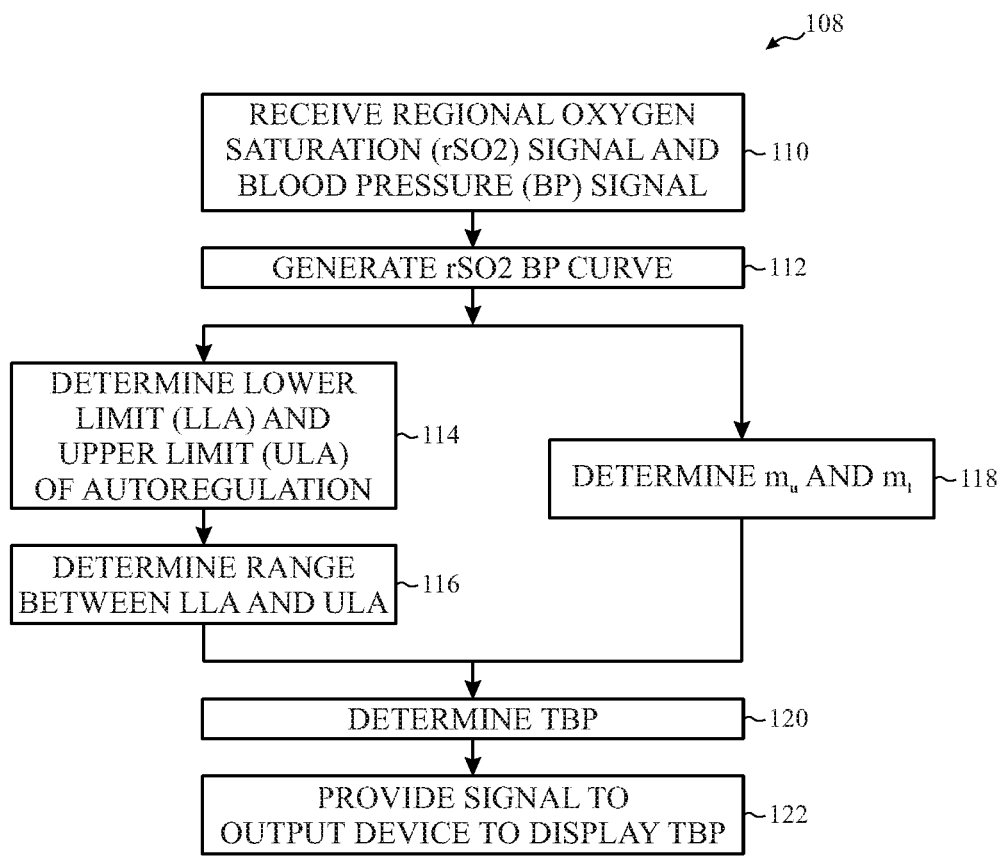
FIG. 8 is a process flow diagram of a method of determining a target blood pressure utilizing characteristics (e.g., gradients) of an $rSO_2$-BP curve derived from regional oxygen saturation values and blood pressure values, in accordance with an embodiment.

FIG. 8 is a process flow diagram of a method 108 of determining the TBP utilizing characteristics (e.g., gradients or error size) of the $rSO_2$-BP curve 92 derived from regional oxygen saturation values and blood pressure values. The method 108 includes various steps represented by blocks. The method 108 may be performed as an automated procedure by a system, such as system 10. For example, some or all of the steps of the method 108 may be implemented by the controller 16 (e.g., the processor 24 of the controller 16). Although the flow chart illustrates the steps in a certain sequence, it should be understood that the steps may be performed in any suitable order, certain steps may be carried out simultaneously, and/or certain steps may be omitted, where appropriate. In addition, insofar as steps of the method 108 disclosed herein are applied to the received signals, it should be understood that the received signals may be raw signals or processed signals. That is, the method 108 may be applied to an output of the received signals.

In step 110, the controller 16 may receive the blood pressure signal (e.g., arterial blood pressure signal) and the regional oxygen saturation signal. In some embodiments, the controller 16 may receive the blood pressure signal from the blood pressure sensor 12, as set forth above. In some embodiments, the controller 16 may receive the regional oxygen saturation signal from the regional oxygen saturation sensor 14. In step 112, the controller 16 generates the $rSO_2$-BP curve (e.g., rSO2-BP curve 92) from the blood pressure signal and the regional oxygen saturation signal. In step 114, the controller 16 may determine the LLA and ULA from the $rSO_2$-BP curve. In step 116, the controller 16 may determine a blood pressure range between the LLA and ULA. In step 118, the controller 16 may determine the gradients, $m_u$ and $m_l$, from the $rSO_2$-BP curve.

In step 120, the controller 16 may determine the TBP utilizing one or more equations. For example, in embodiments where the TBP is weighted towards the lower gradient, the controller 16 may utilize the following equation:

$$TBP = LLA + RANGE \times (m_u/(m_u + m_l)), \quad (1)$$

where RANGE=ULA−LLA. In embodiments where the TBP is weighted towards the higher gradient, the controller may utilize the following equation:

$$TBP = ULA - RANGE \times (m_u/(m_u + m_l)). \quad (2)$$

As described below, other characteristics of the rSO$_2$-BP curve may be utilized in determining the TBP. In step 122, the controller 16 may provides a signal to the output device 18 to display the TBP as described above.

Figure 9:
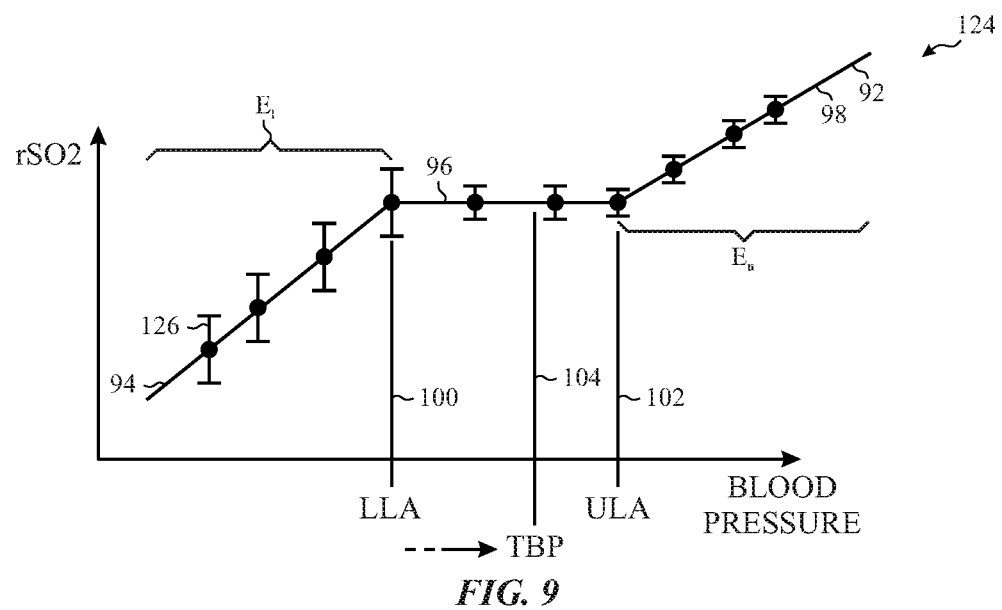
FIG. 9 is an example of a graph illustrating an $rSO_2$-BP curve derived from regional oxygen saturation values and blood pressure values (e.g., having a target blood pressure derived from errors associated with the $rSO_2$-BP curve)

In other embodiments, error bars associated with the curve may be utilized by the controller 16 to determine the TBP. FIG. 9 is an example of a graph 124 illustrating the rSO$_2$-BP curve 92 derived from regional oxygen saturation values and blood pressure values (e.g., having the TBP derived from errors associated with the rSO$_2$-BP curve 92). As depicted, the curve 92 may include error bars 126 associated with different regions of the curve 92. From these error bars 26, a characteristic size of the error, E, may be derived (e.g., E$_l$ for region positive gradient region 94 and E$_u$ for positive gradient portion 98) for each region of the curve 92. E$_l$ and E$_u$ may be determined utilizing a variety of statistics (e.g., standard deviation, mean absolute deviation, mediation absolute deviation, etc.). In embodiments where the TBP is weighted towards the error bars 26 associated with the region 94 below the LLA, the controller 16 may utilize the following equation:

$$TBP = LLA + RANGE \times (E_l/(E_u + E_l)). \quad (3)$$

In embodiments where the TBP is weighted towards the error bars 26 associated with the region 98 about the ULA, the controller 16 may utilize the following equation:

$$TBP = ULA - RANGE \times (E_l/(E_u + E_l)). \quad (4)$$

Figure 10:
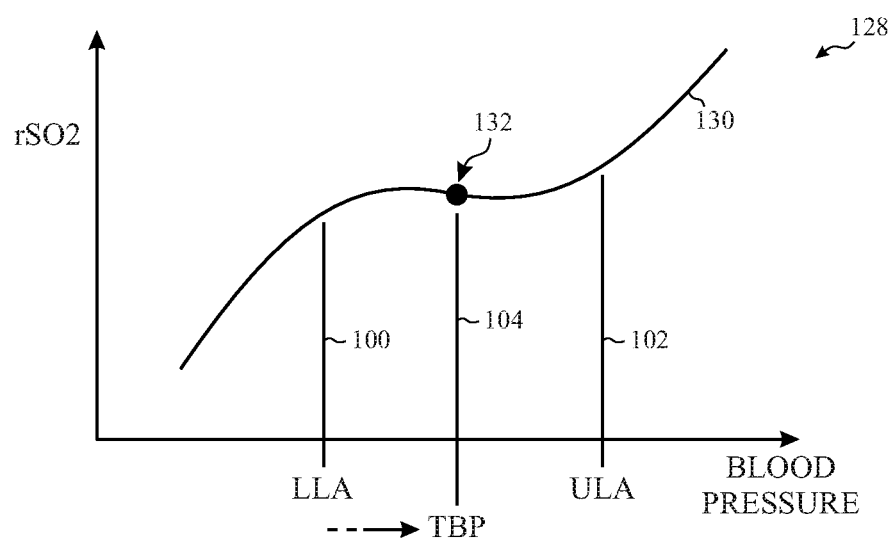
FIG. 10 is an example of a graph illustrating an $rSO_2$-BP curve derived from regional oxygen saturation values and blood pressure values (e.g., having a target blood pressure derived from a point of inflection of the $rSO_2$-BP curve).

In certain embodiments, the rSO$_2$-BP curve may not be ideal for determining the TBP. FIG. 10 is an example of a graph 128 illustrating a non-ideal rSO$_2$-BP curve 130 derived from regional oxygen saturation values and blood pressure values. The curve 130 may include smooth changes as depicted in FIG. 10. In certain embodiments, a second derivative may be taken from the curve 130 to a search for a zero representing the point of inflection. The point of inflection 132 of the curve 130 may be utilized by the controller as the TBP.

In certain embodiments, more complex functions (e.g., time-tangential functions, artificial neural network, etc.) may be utilized by the controller 16 to determine the TBP. In other embodiments, patient specific information (age sex, BMI, etc.) may be utilized as inputs by the controller 16 to determine the TBP.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A monitor for monitoring autoregulation, the monitor comprising:
   a display;
   a memory encoding one or more processor-executable instructions; and
   one or more processors configured to access and execute the one or more instructions encoded by the memory, wherein the instructions, when executed, cause the one or more processors to:
   receive one or more physiological signals from a patient;
   determine a correlation-based measure indicative of an autoregulation of the patient based on the one or more physiological signals;
   generate an autoregulation profile of the patient based on autoregulation index values of the correlation-based measure, wherein the autoregulation profile comprises the autoregulation index values sorted into bins corresponding to different blood pressure ranges;
   designate a blood pressure range encompassing one or more of the bins as a blood pressure safe zone indicative of intact autoregulation;
   provide a first signal to the display to display the autoregulation profile and a first indicator of the blood pressure safe zone; and
   provide a second signal to the display to display a second indicator of a target blood pressure within the blood pressure safe zone for the patient.

2. The monitor of claim 1, wherein the correlation-based measure is one of a cerebral oximetry index, a hemoglobin volume index, or a mean velocity index.

3. The monitor of claim 1, wherein the one or more instructions, when executed, cause the one or more processors to:
   receive patient specific inputs, the patient specific input being physical characteristics of the patient,
   wherein the instructions to designate the blood pressure range encompassing one or more of the bins as the blood pressure safe zone indicative of intact autoregulation comprise instructions to designate the blood pressure range encompassing one or more of the bins as an initial blood pressure safe zone indicative of intact autoregulation utilizing at least historical population data based on the patient specific inputs, and
   wherein the instructions to provide the first signal to the display comprise instructions to provide a signal to display an indicator of the initial blood pressure safe zone.

4. The monitor of claim 3, wherein the instructions to designate the blood pressure range encompassing one or more of the bins as the initial blood pressure safe zone indicative of intact autoregulation comprise instructions to designate the blood pressure range as the initial blood pressure safe zone utilizing both the historical population data based on the patient specific inputs and initially measured baselines of physiological parameters of the patient.

5. The monitor of claim 3, wherein the one or more instructions, when executed, cause the one or more processors to:
   determine if there is sufficient data within the autoregulation profile to designate a patient-specific blood pressure safe zone;
   in response to determining that there is sufficient data, subsequently designate the blood pressure range encompassing one or more of the bins as a subsequent patient specific blood pressure safe zone indicative of intact autoregulation utilizing the autoregulation index values and corresponding blood pressure levels; and
   provide a third signal to the display to display an indicator of the subsequent patient specific blood pressure safe zone.

6. The monitor of claim 5,
   wherein the indicator of the initial blood pressure safe zone comprises a first color, and wherein the indicator of the subsequent patient specific blood pressure safe zone comprises a second color different from the first color.

7. The monitor of claim 1, wherein the one or more instructions, when executed, cause the one or more processors to:
change a color of the second indicator displayed on the display based on a distance of a current blood pressure of the patient derived from the target blood pressure; or
change a level of a blip bar displayed on the display based on the distance of the current blood pressure of the patient derived from the target blood pressure.

8. The monitor of claim 1, wherein the one or more instructions, when executed, cause the one or more processors to receive a user input of the target blood pressure.

9. The monitor of claim 1,
wherein the one or more physiological signals comprise a regional oxygen saturation signal and a blood pressure signal,
wherein the instructions to generate the autoregulation profile comprise instructions to generate a curve from the regional oxygen saturation signal and the blood pressure signal, and
wherein the instructions to designate the blood pressure safe zone comprise instructions to:
determine both a lower limit (LLA) and an upper limit (ULA) of autoregulation from the curve; and
determine the target blood pressure based on the curve.

10. The monitor of claim 9, wherein the instructions to determine the target blood pressure comprise instructions to designate a point equidistant between the LLA and ULA as the target blood pressure.

11. The monitor of claim 9, wherein the one or more instructions, when executed, cause the one or more processors to:
determine a first gradient of the curve at a first blood pressure portion of the curve lower than the LLA; and
determine a second gradient of the curve at a second blood pressure portion of the curve higher than the ULA,
wherein the instructions to determine the target blood pressure comprise instructions to determine the target blood pressure based on the first gradient, the second gradient, or a combination thereof.

12. The monitor of claim 9, wherein the instructions to determine the target blood pressure comprise instructions to designate a point of inflection of the curve as the target blood pressure.

13. The monitor of claim 1, wherein the one or more instructions, when executed, cause the one or more processors to provide a third signal to the display or other output device to provide an audible or visual indication that a current blood pressure of the patient is outside the blood pressure safe zone.

14. The monitor of claim 13,
wherein the audible or visual indication comprises a first audible or visual indication that indicates that the current blood pressure is higher than the blood pressure safe zone and a second audible or visual indication that the current blood pressure is lower than the blood pressure safe zone, and
wherein the first audible or visual indication is different from the second audible or visual indication.

15. The monitor of claim 1, wherein the instructions to provide the first signal to the display comprise instructions to cause the display to flash the autoregulation profile and the first indicator of the blood pressure safe zone on and off.

16. The monitor of claim 1, wherein the instructions to provide the first signal to the display comprise instructions to provide the first signal to the display to display a blood pressure history of the patient, wherein the blood pressure history depicts an amount of time blood pressure measurements within the bins are within the blood pressure safe zone.

17. The monitor of claim 16, wherein the first indicator of the blood pressure safe zone overlays a portion of the autoregulation profile corresponding to the blood pressure safe zone.

18. A method for monitoring autoregulation, the method comprising:
receiving, by one or more processors executing one or more instructions encoded on a memory, one or more physiological signals from a patient;
determining, by the one or more processors, a correlation-based measure indicative of an autoregulation of the patient based on the one or more physiological signals;
generating, by the one or more processors, an autoregulation profile of the patient based on autoregulation index values of the correlation-based measure, wherein the autoregulation profile comprises the autoregulation index values sorted into bins corresponding to different blood pressure ranges;
designating, by the one or more processors, a blood pressure range encompassing one or more of the bins as a blood pressure safe zone indicative of intact autoregulation;
providing, by the one or more processors and to a display, a signal to display the autoregulation profile and a first indicator of the blood pressure safe zone; and
providing, by the one or more processors and to the display, a second signal to display a second indicator of a target blood pressure within the blood pressure safe zone for the patient.

19. A monitor for monitoring autoregulation, the monitor comprising:
a display;
a memory encoding one or more processor-executable instructions; and
one or more processors configured to access and execute the one or more instructions encoded by the memory, wherein the instructions, when executed, cause the one or more processors to:
receive one or more physiological signals from a patient;
determine a correlation-based measure indicative of an autoregulation of the patient based on the one or more physiological signals;
generate an autoregulation profile of the patient based on autoregulation index values of the correlation-based measure, wherein the autoregulation profile comprises the autoregulation index values sorted into bins corresponding to different blood pressure ranges;
determine if there is sufficient data within the autoregulation profile to designate a patient-specific blood pressure safe zone;
in response to determining that there is sufficient data, designate a blood pressure range encompassing one or more of the bins as a patient-specific blood pressure safe zone indicative of intact autoregulation utilizing the autoregulation index values and corresponding blood pressure levels; and provide a first signal to the display to display the autoregulation profile and a first indicator of the patient-specific blood pressure safe zone.

20. The monitor of claim 19, wherein the one or more instructions, when executed, cause the one or more processors to:
   receive patient specific inputs, the patient specific inputs being physical characteristics of the patient;
   in response to determining that there is insufficient data, designate the blood pressure range encompassing one or more of the bins as an initial blood pressure safe zone indicative of intact autoregulation utilizing at least historical population data based on the patient specific inputs; and
   provide a second signal to the display to display an indicator of the initial blood pressure safe zone.

21. The monitor of claim 1, wherein the one or more instructions, when executed, cause the one or more processors to provide a third signal to the display or another output device to provide a visual or audible indication of a distance the current blood pressure is from the target blood pressure.

* * * * *